(12) United States Patent
Shen et al.

(10) Patent No.: US 10,463,741 B2
(45) Date of Patent: Nov. 5, 2019

(54) NON-GELATIN VACCINE PROTECTANT COMPOSITION AND LIVE ATTENUATED INFLUENZA VACCINE

(71) Applicant: Changchun BCHT Biotechnology Co., Changchun (CN)

(72) Inventors: Zhenwei Shen, Changchun (CN); Xiaohui Chen, Changchun (CN); Fei Xu, Changchun (CN); Yao Sun, Changchun (CN); Xiaogeng Cheng, Changchun (CN); Changlin Zhu, Changchun (CN); Chunlai Jiang, Changchun (CN); Wei Kong, Changchun (CN)

(73) Assignee: Changchun BCHT Biotechnology Co., Changchun (CN)

( * ) Notice: Subject to any disclaimer, the term of this patent is extended or adjusted under 35 U.S.C. 154(b) by 0 days.

(21) Appl. No.: 15/578,124

(22) PCT Filed: Apr. 26, 2016

(86) PCT No.: PCT/CN2016/080226
§ 371 (c)(1),
(2) Date: Nov. 29, 2017

(87) PCT Pub. No.: WO2016/192487
PCT Pub. Date: Dec. 8, 2016

(65) Prior Publication Data
US 2018/0154004 A1    Jun. 7, 2018

(30) Foreign Application Priority Data

Jun. 2, 2015   (CN) .......................... 2015 1 0296497

(51) Int. Cl.
| | | |
|---|---|---|
| *A61K 47/42* | (2017.01) | |
| *A61K 39/145* | (2006.01) | |
| *A61K 47/12* | (2006.01) | |
| *A61K 47/16* | (2006.01) | |
| *A61K 47/18* | (2017.01) | |
| *A61K 47/22* | (2006.01) | |
| *A61K 47/26* | (2006.01) | |
| *A61K 39/12* | (2006.01) | |

(Continued)

(52) U.S. Cl.
CPC ............ *A61K 47/42* (2013.01); *A61K 9/0019* (2013.01); *A61K 9/08* (2013.01); *A61K 39/12* (2013.01); *A61K 39/145* (2013.01); *A61K 47/12* (2013.01); *A61K 47/16* (2013.01); *A61K 47/183* (2013.01); *A61K 47/22* (2013.01); *A61K 47/26* (2013.01); *A61K 2039/5254* (2013.01); *A61K 2039/54* (2013.01); *A61K 2039/543* (2013.01); *A61K 2039/70* (2013.01); *C12N 2760/16134* (2013.01); *C12N 2760/16234* (2013.01)

(58) Field of Classification Search
CPC ............ C12N 7/00; C12N 2760/16251; C12N 2760/16234; C12N 1/04; C12N 2760/16051; C12N 2760/16134; C12N 2760/16034; C12N 2760/16071; A61K 39/12; A61K 39/145; A61K 2039/6081; A61K 2300/00; A61K 39/00; A61K 2039/6075; A61K 39/39516; A61K 47/643; A61K 35/76; A61K 38/385; A61K 47/42; A61K 9/08; A61K 9/0019; A61K 47/12; A61K 47/16; A61K 47/183; A61K 47/22; A61K 47/26; A61K 2039/70; A61K 2039/543; A61K 2039/5254; A61K 2039/54; C07K 2317/76; C07K 2317/21; C07K 16/1018; C07K 14/005; C07K 14/765

See application file for complete search history.

(56) References Cited

U.S. PATENT DOCUMENTS

| | | |
|---|---|---|
| 6,231,860 B1 | 5/2001 | Fanget et al. |
| 7,620,795 B1 | 11/2009 | Ryser |

(Continued)

FOREIGN PATENT DOCUMENTS

| | | |
|---|---|---|
| CN | 1209067 A | 2/1999 |
| CN | 1927395 A | 3/2007 |

(Continued)

OTHER PUBLICATIONS

English machine translation of CN101537186A. Sep. 2009.*

(Continued)

*Primary Examiner* — Rachel B Gill
(74) *Attorney, Agent, or Firm* — Leydig, Voit & Mayer, Ltd.

(57) ABSTRACT

The present invention provides a composition for use as the protectant for a live attenuated influenza virus vaccine, comprising the following components at the following concentrations: human serum albumin: 1.0-15.0 g/L, sugar: 15.0-95.0 g/L, and sodium glutamate: 0.5-15.0 g/L. The present invention also provides a process for preparing a live attenuated influenza vaccine with the composition according to the present invention, comprising the following steps: dissolving the components of the composition according to the present invention sequentially into a pH buffer solution, adjusting the pH to a specified value, performing filtration sterilization, and adding virus stock to give the live attenuated influenza vaccine. The present invention further provides a live attenuated influenza vaccine, which may be used as an injection or nasal spray.

4 Claims, No Drawings

(51) Int. Cl.
  *A61K 9/00* (2006.01)
  *A61K 9/08* (2006.01)
  *A61K 39/00* (2006.01)

(56) References Cited

U.S. PATENT DOCUMENTS

| | | | |
|---|---|---|---|
| 9,598,676 B2 * | 3/2017 | Vadrevu | A61K 39/15 |
| 2014/0302091 A1 * | 10/2014 | Stinchcomb | A61K 39/12 424/218.1 |
| 2016/0051660 A1 * | 2/2016 | Trager | A61K 39/145 424/186.1 |
| 2016/0220483 A1 * | 8/2016 | Mistilis | A61K 9/0021 |

FOREIGN PATENT DOCUMENTS

| | | | | |
|---|---|---|---|---|
| CN | 101060859 A | | 10/2007 | |
| CN | 101537186 A | | 9/2009 | |
| CN | 101537186 A | * | 9/2009 | A61K 9/19 |
| CN | 102202688 A | | 9/2011 | |
| CN | 102302773 A | | 1/2012 | |
| CN | 103472235 A | | 12/2013 | |
| CN | 104258404 A | | 1/2015 | |
| CN | 104383550 A | | 3/2015 | |
| CN | 104640566 A | | 5/2015 | |
| EP | 0 781 144 A1 | | 7/1997 | |
| EP | 1129723 A1 | | 9/2001 | |
| WO | WO 1996/008273 A1 | | 3/1996 | |
| WO | WO 1997/023238 A1 | | 7/1997 | |
| WO | 1999/12568 | | 3/1999 | |
| WO | WO-9912568 A1 | * | 3/1999 | A61K 39/165 |
| WO | 2003/087327 | | 10/2003 | |
| WO | 2006/041819 | | 4/2006 | |
| WO | WO 2006/041819 A1 | | 4/2006 | |
| WO | WO 2010/124428 A1 | | 11/2010 | |
| WO | WO 2010/146598 A2 | | 12/2010 | |
| WO | WO 2014/029702 A1 | | 2/2014 | |
| WO | 2015/034924 | | 3/2015 | |
| WO | WO-2018027075 A1 | * | 2/2018 | A61K 39/12 |
| WO | WO-2018041891 A1 | * | 3/2018 | A61K 39/12 |

OTHER PUBLICATIONS

International Search Report with Written Opinion corresponding to International Patent Application No. PCT/CN2016/080226, dated Jun. 29, 2016.

First Office Action with Search Report corresponding to Chinese Patent Application No. 201510296497.0—provided with English translation only.

Second Office Action with Search Report corresponding to Chinese Patent Application No. 201510296497.0—provided with English translation only.

Chinese First Office Action, dated Jun. 28, 2017, and First Search Report in Chinese Patent Application No. 201510296497.0, a related application, 18 pp. (with English translation).

Chinese Second Office Action, dated Sep. 27, 2017, and Second Search Report in Chinese Patent Application No. 201510296497.0, a related application, 18 pp. (with English translation).

European Extended Search Report, dated Oct. 25, 2018, corresponding to European Application No. 16802410.7, a related application, 8 pp.

* cited by examiner

NON-GELATIN VACCINE PROTECTANT COMPOSITION AND LIVE ATTENUATED INFLUENZA VACCINE

CROSS-REFERENCE TO RELATED APPLICATIONS

This application is a U.S. National Stage Application filed under 35 U.S.C. § 371 of International Application No. PCT/CN2016/080226, filed Apr. 26, 2016, which claims the benefit of Chinese Application No. 201510296497.0, filed Jun. 2, 2015. Both of these applications are hereby incorporated by reference in their entireties.

TECHNICAL FIELD

The present invention belongs to the technical field of a process for producing vaccines, and specifically, relates to a gelatin-free protectant composition for a liquid vaccine, and a live attenuated influenza vaccine comprising the same.

BACKGROUND OF THE INVENTION

Influenza is an acute respiratory infectious disease that is caused by influenza virus and could seriously harm the health of human beings. Influenza viruses include three types of (A), (B) and (C), wherein the antigenicity of influenza A virus varies a lot, and has multiple times caused global pandemic in history. Influenza virus A also spreads among pigs and birds, and causes influenza pandemic and the death of numerous animals, while human influenza virus B and human influenza virus C only spread among human beings. Influenza virus B is of low pathogenicity against human beings, and Influenza virus C mainly attacks infants and children, and usually cannot cause influenza epidemic. According to the estimation of WHO, during the explosive epidemic of influenza, the influenza viruses could rapidly spread over the whole world, and affect 10%-20% of the whole population. Even in the years of non-explosive influenza epidemic, they would bring about 3 to 5 million serious cases and 250 to 500 thousand deaths each year.

So far, influenza vaccination is the most effective means for controlling influenza. The vaccination against influenza could not only reduce the incidence and death rate of high-risk population, but also could alleviate symptoms and reduce the occurrence rate of complications and the possibility of transmission.

Live attenuated influenza vaccines are immunized via the route of nasal mucosa, and has the advantage of mimicking natural infection. As compared with inactivated vaccines, live attenuated influenza vaccines, in addition to inducing humoral immunity, could also induce local neutralizing antibody and cellular immune response, which lasts for a long time. In addition, live attenuated influenza vaccines are easy to use, and are easily to be immunized in large scale.

Live attenuated influenza vaccines are usually formulated into freeze-dried powder injection. Although free-drying technique is mature, it still has the following defects: first, free-dried powder injection needs to be reconstituted before use, which is not easy to use and increases the possibility of being polluted; second, the freeze-drying process of biological products is complicated and time-consuming, and causes big loss of influenza virus titer; and third, vacuum freeze-drying equipment requires large investment, high energy consumption and high costs, but has limited vaccine production capacity, and especially in the outbreak of influenza, it is difficult for the vaccine manufacturers to produce sufficient doses of vaccine in a short time.

In 2003, MedImmune Company's attenuated influenza vaccine, FluMist, was approved by FDA. The product is a cold-adapted trivalent viral vaccine, and is an aqueous solution for injection. The product needs to be stored and transported at a temperature of about 15° C. and below, which limits the large-scale application of FluMist because pharmacies or schools usually do not have the equipment for handling frozen products.

In 2005, MedImmune Vaccines Inc. filed a patent application entitled "Refrigerator-Temperature Stable Influenza Vaccine Compositions" (Patent Application No. PCT/US2005/035614), providing liquid formulations comprising a hydrolyzed gelatin component that can stabilize the influenza vaccine at temperatures ranging from 4° C. to 8° C. Nevertheless, the gelatin or gelatin derivatives in the formulations can directly cause allergy and non-cellular mediated immune responses in vaccines.

Therefore, in order to overcome the defects of the high cost in freeze-drying technology and the allergic reaction and immune response that are easily caused by hydrolyzed gelatin component, there is need to develop a gelatin-free protectant for a liquid vaccine formulation and a live attenuated influenza vaccine containing the same.

SUMMARY OF THE INVENTION

After conducting research, the inventor invented a composition for use as the protectant for a live attenuated influenza vaccine. Said composition does not comprise gelatin component and is less irritating to human body. Moreover, the live attenuated influenza vaccine formulated with said composition could keep good stability and long shelf life under refrigerated conditions.

Thus, the present invention provides a composition for use as the protectant for a live attenuated influenza vaccine, comprising the following components at the following concentrations:

human serum albumin: 1.0-15.0 g/L, preferably 1.5-12.0 g/L, more preferably 2.5-10.0 g/L; sucrose: 15.0-95.0 g/L, preferably 40.0-85.0 g/L, more preferably 50.0-75.0 g/L; and sodium glutamate: 0.5-15.0 g/L, preferably 0.5-12.0 g/L, more preferably 0.5-10.0 g/L; wherein the composition has a pH of 5.0-9.0, preferably a pH of 5.5-8.5, more preferably a pH of 6.0-8.0, most preferably a pH of 6.0-7.4.

The composition according to the present invention further comprises: urea at a concentration of 0-8.0 g/L, preferably 0.5-6.0 g/L, more preferably 1.0-4.0 g/L; arginine at a concentration of 0-10.0 g/L, preferably 1.0-10.0 g/L, more preferably 1.4-10.0 g/L; histidine at a concentration of 0-2.0 g/L, preferably 0.5-1.5 g/L; sorbitol at a concentration of 0-70.0 g/L, preferably 15.0-60.0 g/L, more preferably 25.0-50.0 g/L; glycine at a concentration of 0-20.0 g/L, preferably 3.0-15.0 g/L; and mannitol at a concentration of 0-30.0 g/L, preferably 10.0-20.0 g/L.

The present invention further provides the use of the composition according to the invention for improving the stability and safety of vaccine and the use for preparing a live influenza virus vaccine.

Additionally, the present invention further provides a process for preparing a live attenuated influenza vaccine, wherein the composition according to the present invention is used as the protectant.

DETAILED DESCRIPTION OF THE INVENTION

The present invention provides a composition for use as the protectant for a live attenuated influenza vaccine, comprising the following components at the following concentrations:

human serum albumin: 1.0-15.0 g/L, preferably 1.5-12.0 g/L, more preferably 2.5-10.0 g/L; sucrose: 15.0-95.0 g/L, preferably 40.0-85.0 g/L, more preferably 50.0-75.0 g/L; and sodium glutamate: 0.5-15.0 g/L, preferably 0.5-12.0 g/L, more preferably 0.5-10.0 g/L; wherein the composition has a pH of 5.0-9.0, preferably a pH of 5.5-8.5, more preferably a pH of 6.0-8.0, most preferably a pH of 6.0-7.4.

The composition according to the present invention further comprises urea at a concentration of 0-8.0 g/L, preferably 0.5-6.0 g/L, more preferably 1.0-4.0 g/L; arginine at a concentration of 0-10.0 g/K, preferably 1.0-10.0 g/L, more preferably 1.4-10.0 g/L; histidine at a concentration of 0-2.0 g/L, preferably 0.5-1.5 g/L; sorbitol at a concentration of 0-70.0 g/L, preferably 15.0-60.0 g/L, more preferably 25.0-50.0 g/L; glycine at a concentration of 0-20.0 g/L, preferably 3.0-15.0 g/L; and mannitol at a concentration of 0-30.0 g/L, preferably 10.0-20.0 g/L.

The present invention further provides the use of the composition according to the present invention for preparing live influenza virus vaccine.

The present invention additionally provides a process for preparing a live attenuated influenza vaccine, wherein the composition according to the present invention is used as the protectant.

In a preferred embodiment, the process for preparing a live attenuated influenza vaccine according to the invention comprises the following steps: dissolving the components of the composition according to the present invention sequentially into a pH buffer solution, adjusting the pH to a specified value, performing filtration sterilization, and adding virus stock to give the live attenuated influenza vaccine.

In a preferred embodiment, the liquid live attenuated influenza vaccine prepared according to the process of the present invention has a pH of 5.0-9.0, preferably a pH of 5.5-8.5, more preferably a pH of 6.0-8.0, most preferably a pH of 6.0-7.4.

In a preferred embodiment, phosphate buffer is used as the pH buffer solution.

The present invention further provides a live attenuated influenza vaccine, which uses the composition according to the present invention and/or is prepared according to the process according to the present invention.

In a preferred embodiment, the live attenuated influenza vaccine according to the present invention is an injection or nasal spray.

The present invention would be further illustrated by the following examples.

Example 1

1. Determination of the pH Value

The pH value is determined according to Appendix V A of Pharmacopoeia of People's Republic of China (2010 edition) (the third volume).

2. Determination of the Virus Titer

Cell Line:

MDCK cells: Madin-Baby canine kidney cells, commercially available from ATCC.

Virus Strains:

H1N1 influenza virus strain: A/17/California/2009/38 (H1N1), provided by WHO;

H3N2 influenza virus strain: A/17/Perth/09/87(H3N2), provided by WHO;

Influenza B virus strain: B/56/Brisbane/60/08, provided by WHO.

Reagents:

TPCK-Trypsin (commercially available from Sigma, article number: T1426) solution;

DMEM cell-culture medium (commercially available from Sigma, article number: D6546);

Fetal Bovine Serum (commercially available from Hyclone, article number: SH30070.03);

L-glutamine (commercially available from Gibco, article number: 25030) solution;

Mycillin (commercially available from Gibco, article number: 15140);

HEPES (commercially available from JINUO BIOLOGY, article number: GNM11344) solution;

Primary Antibody: Anti-Influenza A virus Nucleoprotein antibody, commercially available from Abcam, article number: [AA5H] ab20343;

Anti-Influenza B Virus Nucleoprotein antibody, commercially available from Abcam, article number: [B017] ab20711;

Secondary Antibody: Alexa Fluor® 488 Goat Anti-Mouse IgG (H+L) Antibody, commercially available from Lifetechnologies, article number: A-11001;

Standard Antibody:

Anti-A1 standard antibody: Influenza Anti-A/California/7/2009(H1N1)-HA Serum, commercially available from NIBSC, article number: 12/108;

Anti-A3 standard antibody: Influenza Anti-A/Perth/16/2009-Like HA Serum, commercially available from NIBSC, article number: 11/206;

Anti-B standard antibody: Influenza Anti-B-Brisbane/60/2008 HA serum, commercially available from NIBSC, article number: 11/136.

Method:

(1) Sample Processing

Three bottles of test samples were mixed and used as samples to be tested.

The deactivated standard antibodies were classified into the following three groups:

G1: 1 part of anti-A3 standard antibody+1 part of anti-B standard antibody+3 parts of PBS;

G2: 1 part of anti-A1 standard antibody+1 part of anti-B standard antibody+3 parts of PBS; and G3: 1 part of anti-A1 standard antibody+1 part of anti-A3 standard antibody+3 parts of PBS.

The three groups of antibodies G1, G2 and G2 were respectively mixed with the samples to be tested at a ratio of 1:1, and The thus obtained solutions were kept at 32° C. for 30 minutes and to be used as virus samples.

(2) Determination of the Titer

MDCK cells in good growth state were laid and cultured on a 96-cell plate until they overspread the whole 96-cell plate. Cell growth medium in the plate was abandoned, and DMEM was added for washing the plate; the washed plate was ready for use. The virus samples were diluted to an appropriate concentration through a series of 10-fold dilutions. Then, the diluted virus samples were inoculated in a 96-cell plate and incubated in a 5% $CO_2$ cell incubators at a temperature of 37° C., and were taken out after 17-20 hours of incubation. The cells were fixed with 80% (v/v) acetone at about a temperature of 20° C. The fixed cells were then washed twice with 0.5% TPBS. The primary antibody was added and inoculated with the cells in a 5% CO2 incubator at a temperature of 37° C. for 1 h. After the primary antibody was removed out, the plate was washed with PBS. Subsequently, the secondary antibody was added, inoculated with the cells in a 5% CO2 incubator at a temperature of 37° C. for 1 h. After the secondary antibody was removed, the plate was washed with PBS. Fluorescent focuses were observed with a fluorescence microscope.

Calculation of the virus titer: observed under 100× microscope, virus titer (1 g FFU/0.2 ml)=2.8×10× the dilution of the virus×the average number of the fluorescent focuses observed in each parallel cell under this concentration.

Unless otherwise indicated, the substances or materials, and the apparatuses used in the following examples are all from the same source and of the same type as those used in example 1.

Example 2

The vaccines according to the present invention were formulated by the following methods:

5.0 g of sucrose, 0.5 g of sodium glutamate, 1.5 ml of human serum albumin (with a mass fraction of 20%) were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A1.

5.0 g of sucrose, 0.5 g of sodium glutamate, 1.5 ml of human serum albumin, and 0.2 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A2.

5.0 g of sucrose, 0.5 g of sodium glutamate, 1.5 ml of human serum albumin, and 0.3 g of glycine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A3.

5.0 g of sucrose, 0.5 g of sodium glutamate, 1.5 ml of human serum albumin, and 0.2 g of histidine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2. influenza virus stock and 10 ml of influenza B virus stock were added to formulate Vaccine A4.

5.0 g of sucrose, 0.5 g of sodium glutamate, 1.5 ml of human serum albumin, and 1.0 g of sorbitol were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A5.

5.0 g of sucrose, 0.5 g of sodium glutamate, 1.5 ml of human serum albumin, and 1.0 g of mannitol were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A6.

5.0 g of sucrose, 0.5 g of sodium glutamate, 1.5 ml of human serum albumin, and 0.5 g of urea were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine A7.

Vaccines A1-A7 were stored under a temperature of 25° C. and sampled respectively at day 0, 14, 21 and 28. The appearance of the samples was inspected and the pH and virus titer thereof were determined according to the method of example 1.

TABLE 1

Stability Results of Vaccines A1-A7 stored at a temperature of 25° C.

| Sample No. | Inspection Item | | Storage Period (day) 0 | 14 | 21 | 28 |
|---|---|---|---|---|---|---|
| A1 | Appearance | | slight milky white | slight milky white | slight milky white | slight milky white |
| | Titer | H1N1 | 7.56 | 6.12 | 5.68 | 4.58 |
| | | H3N2 | 7.33 | 5.67 | 5.40 | 4.50 |
| | | B | 7.26 | 5.42 | 5.08 | 4.20 |
| A2 | Appearance | | slight milky white | slight milky white | slight milky white | slight milky white |
| | Titer | H1N1 | 7.45 | 6.22 | 5.36 | 4.46 |
| | | H3N2 | 7.53 | 6.00 | 5.58 | 4.67 |
| | | B | 7.3 | 5.63 | 5.11 | 4.32 |
| A3 | Appearance | | slight milky white | slight milky white | slight milky white | slight milky white |
| | Titer | H1N1 | 7.52 | 5.83 | 5.28 | 4.72 |
| | | H3N2 | 7.55 | 5.71 | 5.25 | 4.46 |
| | | B | 7.16 | 5.64 | 5.00 | 4.21 |

TABLE 1-continued

Stability Results of Vaccines A1-A7 stored at a temperature of 25° C.

| Sample No. | Inspection Item | | Storage Period (day) | | | |
|---|---|---|---|---|---|---|
| | | | 0 | 14 | 21 | 28 |
| A4 | Appearance | | slight milky white | slight milky white | slight milky white | slight milky white |
| | Titer | H1N1 | 7.48 | 4.12 | 2.20 | 0 |
| | | H3N2 | 7.25 | 3.83 | 2.00 | 0 |
| | | B | 7.24 | 3.56 | 2.22 | 0 |
| A5 | Appearance | | slight milky white | slight milky white | slight milky white | slight milky white |
| | Titer | H1N1 | 7.35 | 6.04 | 4.98 | 4.67 |
| | | H3N2 | 7.58 | 5.92 | 5.37 | 4.58 |
| | | B | 7.27 | 5.64 | 4.92 | 4.53 |
| A6 | Appearance | | slight milky white | slight milky white | slight milky white | slight milky white |
| | Titer | H1N1 | 7.61 | 5.42 | 5.36 | 4.69 |
| | | H3N2 | 7.50 | 5.76 | 5.53 | 4.63 |
| | | B | 7.23 | 5.72 | 5.23 | 4.33 |
| A7 | Appearance | | slight milky white | slight milky white | slight milky white | slight milky white |
| | Titer | H1N1 | 7.38 | 5.53 | 5.47 | 4.79 |
| | | H3N2 | 7.42 | 5.67 | 5.62 | 4.67 |
| | | B | 7.31 | 6.04 | 5.16 | 4.27 |

Example 3

The vaccines according to the present invention were formulated by the following methods:

2.5 g of sucrose, 0.1 g of sodium glutamate, 1.5 ml of human serum albumin, and 0.2 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B1.

2.5 g of sucrose, 0.5 g of sodium glutamate, 3.0 ml of human serum albumin, and 0.5 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B2.

2.5 g of sucrose, 1.0 g of sodium glutamate, 5.0 ml of human serum albumin, and 1.0 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B3.

5.0 g of sucrose, 0.1 g of sodium glutamate, 3.0 ml of human serum albumin, and 1.0 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B4.

5.0 g of sucrose, 0.5 g of sodium glutamate, 5.0 ml of human serum albumin, and 0.2 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate a Vaccine B5.

5.0 g of sucrose, 1.0 g of sodium glutamate, 1.5 ml of human serum albumin, and 0.5 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B6.

7.5 g of sucrose, 0.1 g of sodium glutamate, 5.0 ml of human serum albumin, and 0.5 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B7.

7.5 g of sucrose, 0.5 g of sodium glutamate, 1.5 ml of human serum albumin, and 1.0 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B8.

7.5 g of sucrose, 1.0 g of sodium glutamate, 3.0 ml of human serum albumin, and 0.2 g of arginine were weighed, dissolved in an appropriate amount of phosphate buffer, and subsequently set to a constant volume of 70 ml. The thus obtained solution was adjusted to pH 7.2 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine B9.

Vaccines B1-B9 were stored under a temperature of 25° C. and sampled respectively at day 0, 14, 21 and 28. The appearance of the samples was inspected and the pH and virus titer thereof were determined according to the method of example 1.

1.0 g of mannitol, and 0.4 g of urea were weighed, dissolved in an appropriate amount of phosphate buffer, and subsequently set to a constant volume of 70 ml. The thus obtained solution was adjusted to pH 6.8 with 0.1 N HCl, and then subjected to filtration sterilization with a filter of 0.22 μm. After sterilization, 10 ml of H1N1 influenza virus stock, 10

TABLE 2

Stability Results of Vaccines B1-B9 stored at a temperature of 25° C.

| Sample No. | Inspection Item | | Storage Period (day) | | | |
|---|---|---|---|---|---|---|
| | | | 0 | 14 | 21 | 28 |
| B1 | Appearance | | slight milky white | slight milky white | slight milky white | slight milky white |
| | Titer | H1N1 | 7.38 | 6.06 | 5.66 | 3.67 |
| | | H3N2 | 7.42 | 6.36 | 5.67 | 4.08 |
| | | B | 7.26 | 6.00 | 5.46 | 3.72 |
| B2 | Appearance | | slight milky white | slight milky white | slight milky white | slight milky white |
| | Titer | H1N1 | 7.34 | 6.24 | 5.60 | 4.01 |
| | | H3N2 | 7.58 | 6.20 | 5.50 | 3.90 |
| | | B | 7.17 | 6.15 | 5.60 | 4.10 |
| B3 | Appearance | | slight milky white | slight milky white | slight milky white | slight milky white |
| | Titer | H1N1 | 7.42 | 5.98 | 5.56 | 3.55 |
| | | H3N2 | 7.33 | 5.94 | 5.09 | 3.50 |
| | | B | 7.33 | 5.88 | 5.39 | 3.53 |
| B4 | Appearance | | slight milky white | slight milky white | slight milky white | slight milky white |
| | Titer | H1N1 | 7.35 | 6.39 | 5.55 | 4.10 |
| | | H3N2 | 7.25 | 6.29 | 5.58 | 3.92 |
| | | B | 7.13 | 6.13 | 5.47 | 3.74 |
| B5 | Appearance | | slight milky white | slight milky white | slight milky white | slight milky white |
| | Titer | H1N1 | 7.29 | 6.14 | 5.53 | 3.69 |
| | | H3N2 | 7.34 | 6.12 | 5.36 | 3.82 |
| | | B | 7.30 | 6.13 | 5.50 | 3.86 |
| B6 | Appearance | | slight milky white | slight milky white | slight milky white | slight milky white |
| | Titer | H1N1 | 7.21 | 6.16 | 5.52 | 3.80 |
| | | H3N2 | 7.11 | 5.98 | 5.22 | 3.75 |
| | | B | 7.27 | 5.92 | 5.43 | 3.56 |
| B7 | Appearance | | slight milky white | slight milky white | slight milky white | slight milky white |
| | Titer | H1N1 | 7.53 | 6.19 | 5.51 | 3.83 |
| | | H3N2 | 7.42 | 6.20 | 5.47 | 3.90 |
| | | B | 7.35 | 6.20 | 5.63 | 4.24 |
| B8 | Appearance | | slight milky white | slight milky white | slight milky white | slight milky white |
| | Titer | H1N1 | 7.49 | 6.02 | 5.49 | 3.62 |
| | | H3N2 | 7.21 | 6.15 | 5.41 | 3.83 |
| | | B | 7.29 | 5.82 | 5.35 | 3.49 |
| B9 | Appearance | | slight milky white | slight milky white | slight milky white | slight milky white |
| | Titer | H1N1 | 7.27 | 6.32 | 5.46 | 4.19 |
| | | H3N2 | 7.12 | 6.41 | 5.75 | 4.10 |
| | | B | 7.36 | 6.17 | 5.67 | 4.13 |

Example 4

The vaccines according to the present invention were formulated by the following methods:

7.5 g of sucrose, 0.1 g of sodium glutamate, 3.0 ml of human serum albumin, and 0.5 g of arginine were weighed, dissolved in an appropriate amount of phosphate buffer, and subsequently set to a constant volume of 70 ml. The thus obtained solution was adjusted to pH 6.8 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C1.

7.5 g of sucrose, 0.1 g of sodium glutamate, 3.0 ml of human serum albumin, 0.5 g of arginine, 2.5 g of sorbitol, 1.0 g of mannitol ml of H3N2 influenza virus stock and 10 ml of influenza B virus stock were added to formulate Vaccine C2.

7.5 g of sucrose, 0.1 g of sodium glutamate, 3.0 ml of human serum albumin, 0.5 g of arginine, 5.0 g of sorbitol, 2.0 g of mannitol and 0.8 g of urea were weighed, dissolved in an appropriate amount of phosphate buffer, and subsequently set to a constant volume of 70 ml. The thus obtained solution was adjusted to pH 6.8 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C3.

7.5 g of sucrose, 0.1 g of sodium glutamate, 3.0 ml of human serum albumin, 0.5 g of arginine, 1.0 g of mannitol and 0.8 g of urea were weighed, dissolved in an appropriate amount of phosphate buffer, and subsequently set to a constant volume of 70 ml. The thus obtained solution was adjusted to pH 7.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C4.

7.5 g of sucrose, 0.1 g of sodium glutamate, 3.0 ml of human serum albumin, 0.5 g of arginine, 2.5 g of sorbitol, and 2.0 g of mannitol were weighed, dissolved in an appropriate amount of phosphate buffer, and subsequently set to a constant volume of 70 ml. The thus obtained solution was adjusted to pH 7.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C5.

7.5 g of sucrose, 0.1 g of sodium glutamate, 3.0 ml of human serum albumin, 0.5 g of arginine, 5.0 g of sorbitol and 0.4 g of urea were weighed, dissolved in an appropriate amount of phosphate buffer, and subsequently set to a constant volume of 70 ml. The thus obtained solution was adjusted to pH 7.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C6.

7.5 g of sucrose, 0.1 g of sodium glutamate, 3.0 ml of human serum albumin, 0.5 g of arginine, 2.0 g of mannitol and 0.4 g of urea were weighed, dissolved in an appropriate amount of phosphate buffer, and subsequently set to a constant volume of 70 ml. The thus obtained solution was adjusted to pH 7.8 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C7.

7.5 g of sucrose, 0.1 g of sodium glutamate, 3.0 ml of human serum albumin, 0.5 g of arginine, 2.5 g of sorbitol and 0.8 g of urea were weighed, dissolved in an appropriate amount of phosphate buffer, and subsequently set to a constant volume of 70 ml. The thus obtained solution was adjusted to pH 7.8 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C8.

7.5 g of sucrose, 0.1 g of sodium glutamate, 3.0 ml of human serum albumin, 0.5 g of arginine, 5.0 g of sorbitol and 1.0 g of mannitol were weighed, dissolved in an appropriate amount of phosphate buffer, and subsequently set to a constant volume of 70 ml. The thus obtained solution was adjusted to pH 7.8 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine C9.

Vaccines C1-C9 were stored under a temperature of 25° C. and sampled respectively at day 0, 14, 21 and 28. The appearance of the samples was inspected and the pH and virus titer thereof were determined according to the method of example 1.

TABLE 3

Stability Results of Vaccines C1-C9 stored at a temperature of 25° C.

| Sample No. | Inspection Item | | Storage Period (day) | | | |
|---|---|---|---|---|---|---|
| | | | 0 | 14 | 21 | 28 |
| C1 | Appearance | | slight milky white | slight milky white | slight milky white | slight milky white |
| | Titer | H1N1 | 7.49 | 7.03 | 6.15 | 5.82 |
| | | H3N2 | 7.03 | 6.83 | 6.12 | 5.67 |
| | | B | 7.29 | 6.22 | 5.83 | 5.22 |
| C2 | Appearance | | slight milky white | slight milky white | slight milky white | slight milky white |
| | Titer | H1N1 | 7.63 | 7.12 | 6.37 | 6.34 |
| | | H3N2 | 7.5 | 6.91 | 6.26 | 6.08 |
| | | B | 7.32 | 6.93 | 6.48 | 6.15 |
| C3 | Appearance | | slight milky white | slight milky white | slight milky white | slight milky white |
| | Titer | H1N1 | 7.27 | 6.96 | 6.15 | 5.76 |
| | | H3N2 | 7.42 | 6.75 | 5.92 | 5.58 |
| | | B | 7.22 | 6.55 | 5.64 | 5.37 |
| C4 | Appearance | | slight milky white | slight milky white | slight milky white | slight milky white |
| | Titer | H1N1 | 7.45 | 6.92 | 5.73 | 5.62 |
| | | H3N2 | 7.25 | 6.23 | 5.58 | 5.50 |
| | | B | 7.33 | 6.87 | 5.83 | 5.57 |
| C5 | Appearance | | slight milky white | slight milky white | slight milky white | slight milky white |
| | Titer | H1N1 | 7.30 | 6.82 | 5.66 | 5.54 |
| | | H3N2 | 7.17 | 6.72 | 5.67 | 5.57 |
| | | B | 7.29 | 6.76 | 6.00 | 5.39 |
| C6 | Appearance | | slight milky white | slight milky white | slight milky white | slight milky white |
| | Titer | H1N1 | 7.13 | 6.88 | 5.65 | 5.54 |
| | | H3N2 | 7.00 | 6.01 | 5.55 | 5.42 |
| | | B | 7.16 | 6.36 | 5.77 | 5.25 |

TABLE 3-continued

Stability Results of Vaccines C1-C9 stored at a temperature of 25° C.

| Sample No. | Inspection Item | | Storage Period (day) | | | |
|---|---|---|---|---|---|---|
| | | | 0 | 14 | 21 | 28 |
| C7 | Appearance | | slight milky white | slight milky white | slight milky white | slight milky white |
| | Titer | H1N1 | 7.44 | 5.5 | 4.16 | 3.55 |
| | | H3N2 | 7.42 | 5.53 | 2.92 | 2.51 |
| | | B | 7.31 | 5.67 | 3.98 | 3.3 |
| C8 | Appearance | | slight milky white | slight milky white | slight milky white | slight milky white |
| | Titer | H1N1 | 7.28 | 5.45 | 3.49 | 2.79 |
| | | H3N2 | 7.36 | 5.42 | 4.08 | 3.52 |
| | | B | 7.28 | 5.56 | 2.75 | 2.45 |
| C9 | Appearance | | slight milky white | slight milky white | slight milky white | slight milky white |
| | Titer | H1N1 | 7.37 | 5.86 | 4.75 | 3.63 |
| | | H3N2 | 7.08 | 5.75 | 4.33 | 3.59 |
| | | B | 7.32 | 5.73 | 4.05 | 3.34 |

Example 5

The vaccines according to the present invention were formulated by the following methods:

7.5 g of sucrose, 0.1 g of sodium glutamate, 3.0 ml of human serum albumin, 0.5 g of arginine, 1.0 g of mannitol, 2.5 g of sorbitol, 0.1 g of urea and 0.3 g of glycine were weighed, dissolved in an appropriate amount of phosphate buffer, and subsequently set to a constant volume of 70 ml. The thus obtained solution was adjusted to pH 6.0 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D1.

7.5 g of sucrose, 0.1 g of sodium glutamate, 3.0 ml of human serum albumin, 0.5 g of arginine, 1.0 g of mannitol, 3.5 g of sorbitol, 0.2 g of urea and 0.9 g of glycine were weighed, dissolved in an appropriate amount of phosphate buffer, and subsequently set to a constant volume of 70 ml. The thus obtained solution was adjusted to pH 6.0 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D2.

7.5 g of sugar, 0.1 g of sodium glutamate, 3.0 ml of human serum albumin, 0.5 g of arginine, 1.0 g of mannitol, 3.5 g of sorbitol, 0.2 g of urea and 0.9 g of glycine were weighed, dissolved in an appropriate amount of phosphate buffer, and subsequently set to a constant volume of 70 ml. The thus obtained solution was adjusted to pH 6.0 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D2.

7.5 g of sucrose, 0.1 g of sodium glutamate, 3.0 ml of human serum albumin, 0.5 g of arginine, 1.0 g of mannitol, 5.0 g of sorbitol, 0.4 g of urea and 1.5 g of glycine were weighed, dissolved in an appropriate amount of phosphate buffer, and subsequently set to a constant volume of 70 ml. The thus obtained solution was adjusted to pH 6.0 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D3.

7.5 g of sucrose, 0.1 g of sodium glutamate, 3.0 ml of human serum albumin, 0.5 g of arginine, 1.0 g of mannitol, 2.5 g of sorbitol, 0.2 g of urea and 1.5 g of glycine were weighed, dissolved in an appropriate amount of phosphate buffer, and subsequently set to a constant volume of 70 ml. The thus obtained solution was adjusted to pH 6.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D4.

7.5 g of sucrose, 0.1 g of sodium glutamate, 3.0 ml of human serum albumin, 0.5 g of arginine, 1.0 g of mannitol, 3.5 g of sorbitol, 0.4 g of urea and 0.3 g of glycine were weighed, dissolved in an appropriate amount of phosphate buffer, and subsequently set to a constant volume of 70 ml. The thus obtained solution was adjusted to pH 6.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D5.

7.5 g of sucrose, 0.1 g of sodium glutamate, 3.0 ml of human serum albumin, 0.5 g of arginine, 1.0 g of mannitol, 5.0 g of sorbitol, 0.1 g of urea and 0.9 g of glycine were weighed, dissolved in an appropriate amount of phosphate buffer, and subsequently set to a constant volume of 70 ml. The thus obtained solution was adjusted to pH 6.3 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D6.

7.5 g of sucrose, 0.1 g of sodium glutamate, 3.0 ml of human serum albumin, 0.5 g of arginine, 1.0 g of mannitol, 2.5 g of sorbitol, 0.4 g of urea and 0.9 g of glycine were weighed, dissolved in an appropriate amount of phosphate buffer, and subsequently set to a constant volume of 70 ml. The thus obtained solution was adjusted to pH 6.7 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D7.

7.5 g of sucrose, 0.1 g of sodium glutamate, 3.0 ml of human serum albumin, 0.5 g of arginine, 1.0 g of mannitol, 3.5 g of sorbitol, 0.1 g of urea and 1.5 g of glycine were weighed, dissolved in an appropriate amount of phosphate buffer, and subsequently set to a constant volume of 70 ml. The thus obtained solution was adjusted to pH 6.7 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D8.

7.5 g of sucrose, 0.1 g of sodium glutamate, 3.0 ml of human serum albumin, 0.5 g of arginine, 1.0 g of mannitol, 5.0 g of sorbitol, 0.2 g of urea and 0.3 g of glycine were weighed, dissolved in an appropriate amount of phosphate buffer, and subsequently set to a constant volume of 70 ml. The thus obtained solution was adjusted to pH 6.7 with 0.1 N HCl, and then subjected to filtration sterilization with a filter of 0.22 μm. After sterilization, 10 ml of H1N1 influenza virus stock, 10 ml of H3N2 influenza virus stock and 10 ml of influenza B virus stock were added to formulate Vaccine D9.

Vaccines D1-D9 were stored under a temperature of 25° C. and sampled respectively at day 0, 14, 21 and 28. The appearance of the samples was inspected and the pH and virus titer thereof were determined according to the method of example 1.

TABLE 4

Stability Results of Vaccines D1-D9 stored at a temperature of 25° C.

| Sample No. | Inspection Item | | Storage Period (day) 0 | 14 | 21 | 28 |
|---|---|---|---|---|---|---|
| D1 | Appearance | | slight milky white | slight milky white | slight milky white | slight milky white |
| | Titer | H1N1 | 7.26 | 7.20 | 7.09 | 6.96 |
| | | H3N2 | 7.35 | 7.26 | 7.18 | 7.01 |
| | | B | 7.35 | 7.19 | 7.04 | 6.88 |
| D2 | Appearance | | slight milky white | slight milky white | slight milky white | slight milky white |
| | Titer | H1N1 | 7.29 | 7.27 | 7.16 | 6.90 |
| | | H3N2 | 7.32 | 7.29 | 7.17 | 7.04 |
| | | B | 7.36 | 7.35 | 7.24 | 7.11 |
| D3 | Appearance | | slight milky white | slight milky white | slight milky white | slight milky white |
| | Titer | H1N1 | 7.18 | 7.16 | 7.05 | 6.95 |
| | | H3N2 | 7.48 | 7.3 | 7.11 | 7.02 |
| | | B | 7.30 | 7.21 | 7.01 | 6.92 |
| D4 | Appearance | | slight milky white | slight milky white | slight milky white | slight milky white |
| | Titer | H1N1 | 7.30 | 7.24 | 7.08 | 6.92 |
| | | H3N2 | 7.54 | 7.42 | 7.31 | 6.97 |
| | | B | 7.28 | 7.17 | 7.09 | 6.84 |
| D5 | Appearance | | slight milky white | slight milky white | slight milky white | slight milky white |
| | Titer | H1N1 | 7.35 | 7.33 | 7.28 | 6.94 |
| | | H3N2 | 7.38 | 7.32 | 7.3 | 6.89 |
| | | B | 7.32 | 7.20 | 7.04 | 6.86 |
| D6 | Appearance | | slight milky white | slight milky white | slight milky white | slight milky white |
| | Titer | H1N1 | 7.32 | 7.26 | 7.15 | 6.88 |
| | | H3N2 | 7.45 | 7.31 | 7.26 | 6.96 |
| | | B | 7.26 | 7.15 | 7.04 | 6.89 |
| D7 | Appearance | | slight milky white | slight milky white | slight milky white | slight milky white |
| | Titer | H1N1 | 7.36 | 7.22 | 7.06 | 6.97 |
| | | H3N2 | 7.28 | 7.13 | 7.05 | 6.61 |
| | | B | 7.22 | 7.08 | 6.95 | 6.53 |
| D8 | Appearance | | slight milky white | slight milky white | slight milky white | slight milky white |
| | Titer | H1N1 | 7.27 | 7.24 | 7.04 | 6.86 |
| | | H3N2 | 7.35 | 7.22 | 7.16 | 6.81 |
| | | B | 7.26 | 7.12 | 6.95 | 6.76 |
| D9 | Appearance | | slight milky white | slight milky white | slight milky white | slight milky white |
| | Titer | H1N1 | 7.33 | 7.23 | 6.98 | 6.65 |
| | | H3N2 | 7.39 | 7.28 | 7.12 | 7.00 |
| | | B | 7.34 | 7.21 | 7.09 | 6.93 |

Vaccines D1-D9 were stored under a temperature of 33° C. and sampled respectively at day 0 and 10. The appearance of the samples was inspected and the pH and virus titer thereof were determined according to the method of example 1.

TABLE 5

Stability Results of Vaccines D1-D9 stored at a temperature of 33° C.

| Sample No. | Inspection Item | | Storage Period (day) 0 | 10 |
|---|---|---|---|---|
| D1 | Appearance | | Slight milky white | Slight milky white |
| | Titer | H1N1 | 7.26 | 6.62 |
| | | H3N2 | 7.35 | 6.64 |
| | | B | 7.35 | 6.47 |
| D2 | Appearance | | Slight milky white | Slight milky white |
| | Titer | H1N1 | 7.29 | 6.44 |
| | | H3N2 | 7.32 | 6.73 |
| | | B | 7.36 | 6.72 |
| D3 | Appearance | | Slight milky white | Slight milky white |
| | Titer | H1N1 | 7.18 | 6.56 |
| | | H3N2 | 7.48 | 6.62 |
| | | B | 7.30 | 6.58 |
| D4 | Appearance | | Slight milky white | Slight milky white |
| | Titer | H1N1 | 7.30 | 6.34 |
| | | H3N2 | 7.54 | 6.49 |
| | | B | 7.28 | 6.28 |
| D5 | Appearance | | Slight milky white | Slight milky white |
| | Titer | H1N1 | 7.35 | 6.55 |
| | | H3N2 | 7.38 | 6.31 |
| | | B | 7.32 | 6.43 |
| D6 | Appearance | | Slight milky white | Slight milky white |
| | Titer | H1N1 | 7.32 | 6.40 |
| | | H3N2 | 7.45 | 6.46 |
| | | B | 7.26 | 6.33 |
| D7 | Appearance | | Slight milky white | Slight milky white |
| | Titer | H1N1 | 7.36 | 6.66 |
| | | H3N2 | 7.28 | 6.24 |
| | | B | 7.22 | 6.25 |
| D8 | Appearance | | Slight milky white | Slight milky white |
| | Titer | H1N1 | 7.27 | 6.38 |
| | | H3N2 | 7.35 | 6.26 |
| | | B | 7.26 | 6.25 |
| D9 | Appearance | | Slight milky white | Slight milky white |
| | Titer | H1N1 | 7.33 | 6.08 |
| | | H3N2 | 7.39 | 6.60 |
| | | B | 7.34 | 6.58 |

Vaccines D1-D9 were stored under a temperature of 2-8° C. and sampled respectively at the end of month 0, 1, 3 and 6. The appearance of the samples was inspected and the pH and virus titer thereof were determined according to the method of example 1.

TABLE 6

Stability Results of Vaccines D1-D9 stored at a temperature of 2-8° C.

| Sample No. | Inspection Item | | Storage Period (month) 0 | 1 | 3 | 6 |
|---|---|---|---|---|---|---|
| D1 | Appearance | | slight milky white | slight milky white | slight milky white | slight milky white |
| | pH | | 6.5 | 6.5 | 6.5 | 6.5 |
| | Titer | H1N1 | 7.26 | 7.21 | 7.17 | 6.96 |
| | | H3N2 | 7.35 | 7.30 | 7.25 | 7.10 |
| | | B | 7.35 | 7.28 | 7.16 | 6.85 |
| D2 | Appearance | | slight milky white | slight milky white | slight milky white | slight milky white |
| | pH | | 6.5 | 6.5 | 6.5 | 6.5 |
| | Titer | H1N1 | 7.29 | 7.19 | 7.10 | 6.94 |
| | | H3N2 | 7.32 | 7.28 | 7.23 | 7.02 |
| | | B | 7.36 | 7.3 | 7.13 | 6.88 |
| D3 | Appearance | | slight milky white | slight milky white | slight milky white | slight milky white |
| | pH | | 6.5 | 6.5 | 6.5 | 6.5 |
| | Titer | H1N1 | 7.24 | 7.20 | 7.12 | 6.89 |
| | | H3N2 | 7.48 | 7.38 | 7.32 | 7.06 |
| | | B | 7.34 | 7.30 | 7.22 | 6.80 |
| D4 | Appearance | | slight milky white | slight milky white | slight milky white | slight milky white |
| | pH | | 6.7 | 6.7 | 6.7 | 6.7 |
| | Titer | H1N1 | 7.32 | 7.28 | 7.18 | 7.00 |
| | | H3N2 | 7.54 | 7.34 | 7.26 | 6.94 |
| | | B | 7.28 | 7.26 | 7.08 | 6.74 |
| D5 | Appearance | | slight milky white | slight milky white | slight milky white | slight milky white |
| | pH | | 6.7 | 6.7 | 6.7 | 6.7 |
| | Titer | H1N1 | 7.37 | 7.24 | 7.16 | 6.92 |
| | | H3N2 | 7.38 | 7.33 | 7.24 | 6.98 |
| | | B | 7.32 | 7.25 | 7.15 | 6.71 |
| D6 | Appearance | | slight milky white | slight milky white | slight milky white | slight milky white |
| | pH | | 6.7 | 6.7 | 6.7 | 6.7 |
| | Titer | H1N1 | 7.37 | 7.22 | 7.15 | 6.98 |
| | | H3N2 | 7.45 | 7.36 | 7.19 | 7.00 |
| | | B | 7.26 | 7.28 | 7.22 | 6.86 |

TABLE 6-continued

Stability Results of Vaccines D1-D9 stored at a temperature of 2-8° C.

| Sample No. | Inspection Item | | Storage Period (month) | | | |
|---|---|---|---|---|---|---|
| | | | 0 | 1 | 3 | 6 |
| D7 | Appearance | | slight milky white | slight milky white | slight milky white | slight milky white |
| | pH | | 6.9 | 6.9 | 6.9 | 6.9 |
| | Titer | H1N1 | 7.31 | 7.15 | 7.08 | 6.93 |
| | | H3N2 | 7.28 | 7.13 | 7.05 | 6.74 |
| | | B | 7.22 | 7.2 | 7.09 | 6.80 |
| D8 | Appearance | | slight milky white | slight milky white | slight milky white | slight milky white |
| | pH | | 6.9 | 6.9 | 6.9 | 6.9 |
| | Titer | H1N1 | 7.41 | 7.17 | 7.09 | 6.90 |
| | | H3N2 | 7.35 | 7.32 | 7.10 | 6.82 |
| | | B | 7.26 | 7.23 | 6.94 | 6.77 |
| D9 | Appearance | | slight milky white | slight milky white | slight milky white | slight milky white |
| | pH | | 6.9 | 6.9 | 6.9 | 6.9 |
| | Titer | H1N1 | 7.33 | 7.26 | 7.14 | 6.92 |
| | | H3N2 | 7.39 | 7.29 | 7.22 | 7.03 |
| | | B | 7.34 | 7.27 | 7.05 | 6.72 |

Obviously, without going beyond the basic technical concept of the present invention, those skilled in the art can carry out other various modifications, replacements or changes according to the above contents of the present invention in view of the common technical knowledge and conventional means in the art. Those skilled in the art could understand that various features of the embodiments according to the present invention described in the present application may be appropriately combined according to requirements.

What is claimed is:

1. A live influenza attenuated vaccine, comprising a protectant and influenza virus stock, wherein the protectant consists of the following components at the following concentrations: Human serum albumin: 1.0-15.0 g/L, sucrose: 15.0-95.0 g/L, sodium glutamate: 0.5-15.0 g/L, urea at a concentration of 0.5-8.0 g/L, arginine at a concentration of 1.0-10.0 g/L, sorbitol at a concentration of 15.0-70.0 g/L, glycine at a concentration of 3.0-20.0 g/L, and mannitol at a concentration of 10.0-30.0 g/L;

wherein the vaccine has a pH of 6.0-8.0; and wherein the human serum albumin is not recombinant human serum albumin.

2. The live influenza attenuated vaccine according to claim 1, wherein the vaccine may be used as an injection or nasal spray.

3. A process for preparing the live attenuated influenza vaccine according to claim 1, comprising the steps of:
  1) dissolving the components of the protectant sequentially into a pH buffer solution,
  2) adjusting the pH to 6.0-8.0,
  3) performing filtration sterilization, and
  4) adding virus stock to give the live attenuated influenza vaccine.

4. The process according to claim 3, wherein phosphate buffer is used as the pH buffer solution.

* * * * *